United States Patent [19]

Gross et al.

[11] Patent Number: 4,938,954

[45] Date of Patent: Jul. 3, 1990

[54] HAIRWAX

[75] Inventors: Paul Gross, Darmstadt; Ernst Flemming, Heusenstamm, both of Fed. Rep. of Germany

[73] Assignee: Wella Aktiengesellschaft, Darmstadt, Fed. Rep. of Germany

[21] Appl. No.: 346,026

[22] PCT Filed: May 30, 1988

[86] PCT No.: PCT/EP88/00483

§ 371 Date: Mar. 24, 1989

§ 102(e) Date: Mar. 24, 1989

[87] PCT Pub. No.: WO89/00845

PCT Pub. Date: Feb. 9, 1989

[30] Foreign Application Priority Data

Jul. 29, 1987 [DE] Fed. Rep. of Germany ....... 3725080

[51] Int. Cl.$^5$ .......................... A61K 7/11; A61K 7/13
[52] U.S. Cl. ........................................ 424/71; 424/70; 514/772; 8/405
[58] Field of Search ............... 424/70, 71; 8/405; 514/772

[56] References Cited

U.S. PATENT DOCUMENTS 2,300,722  7/1969  Wilkes et al. ................... 424/71
3,458,624  2/1943  Courtney ............................ 424/71
4,336,246  6/1982  Leon-Pekarek ................... 424/70

FOREIGN PATENT DOCUMENTS 0172713   2/1986  European Pat. Off. .
A61K7-
11AK7/13 6/1979  Japan .

Primary Examiner—Thurman K. Page
Assistant Examiner—Amy Hulina
Attorney, Agent, or Firm—Michael J. Striker

[57] ABSTRACT

The hairwax comprises a combination of
(a) 10 to 41 percent by weight polyethylene glycol (M.W.=3000 to 5000).
(b) 8 to 25 percent by weight hydrogenated castor oil which is ethoxylated with 40 to 60 moles ethylene oxide,
(c) 36 to 51 percent by weight glycerol and/or ethyl hexanediol and/or polyethylene glycol (M.W.=100 to 300),
(d) 0 to 15 percent by weight water.

Our hairwax may also contain
0 to 6 percent by weight of a cosmetic dyestuff and/or
0 to 25 percent by weight of a pearl-luster pigment. The hairwax can be easily rinsed out of the hair but has good hairstyling properties.

17 Claims, No Drawings

HAIRWAX

BACKGROUND OF THE INVENTION

The invention is directed to a hairwax which can be rinsed out easily with water.

Semisolid compositions for hairstyling have already been known for a long time by the name of bar pomade or brilliantine. These hairstyling compositions are preferably used for treating men's hair and are supposed to ensure that the hair lies smoothly on the head. In addition, these compositions impart a sheen to the hair.

In order to style women's hair, on the other hand, so-called hairwaxes are predominantly used. Since a "fixing" effect is also expected from such hairwaxes, they must have a somewhat more solid consistency than brilliantines or pomades and in particular must have "adhesive" properties (that is, strong cohesive forces).

Hairwaxes are composed, as a rule, of a mixture of solid, semisolid and liquid saturated hydrocarbons such as e.g. petrolatum, solid paraffin or paraffin oils. They have waxlike and adhesive and luster imparting properties and therefore enable a satisfactory hairstyling as well as the treatment and shaping of individual hair strands. However, because of their composition such hairwaxes can only be removed again from the hair with great difficulty. Such hairwaxes are not removable from the hair with water, and even when the hair is washed repeatedly with hair shampoo they are removed only in an unsatisfactory manner, so that the hair becomes unsightly and "greasy" with frequent use.

Brilliantines and bar pomades which are removable with water are described in the literature on the subject, but these compositions do not have the desired hairstyling and fixing properties. Thus, for example, in the "Handbook of Cosmetics and Scents", Volume III (1973), by Hugo Janistyn, page 325, a bar pomade is described which can be washed out with water and comprises 60 percent by weight polyethylene glycol (M.W.=4000) and 40 percent by weight ethyl hexanediol. However, as comparison tests show (see Example 7), strands of hair which are treated with such a bar pomade composed in this matter have neither a satisfactory luster nor a sufficient shaping stability or satisfactory non-sag properties.

SUMMARY OF THE INVENTION

Accordingly, it is an object of our invention to provide a hairwax which can be rinsed out easily with water and which enables a good hairstyling and individual treatment of individual strands of hair in the same manner as the previously known hairwaxes.

Surprisingly, it has now been found that a hairwax which is characterized in that it contains a combination of (a) 10 to 41 percent by weight polyethylene glycol with a molecular weight of 3000 to 5000,
(b) 8 to 25 percent by weight hydrogenated castor oil which is ethoxylated with 40 to 60 moles ethylene oxide,
(c) 36 to 51 percent by weight glycerol and/or ethyl hexanediol and/or polyethylene glycol with a molecular weight of 100 to 300 and
(d) 0 to 15 percent by weight water meets the proposed object in an outstanding manner.

A preferred embodiment form of the invention is a hairwax containing a combination of (a) 32 to 41 percent by weight polyethylene glycol with a molecular weight of 3000 to 5000,
(b) 8 to 25 percent by weight hydrogenated castor oil which is ethoxylated with 40 to 45 moles ethylene oxide,
(c) 36 to 51 percent by weight glycerol and/or ethyl hexanediol and/or polyethylene glycol with a molecular weight of 100 to 300 and
(d) 0 to 10 percent by weight water.

Another preferred embodiment form of the invention is a hairwax containing a combination of (a) 10 to 32 percent by weight polyethylene glycol with a molecular weight of 3000 to 5000,
(b) 8 to 25 percent by weight hydrogenated castor oil which is ethoxylated with 40 to 45 moles ethylene oxide,
(c) 36 to 51 percent by weight glycerol and/or ethyl hexanediol and/or polyethylene glycol with a molecular weight of 100 to 300,
(d) 0 to 15 percent by weight water and
(e) 5 to 25 percent by weight of a pearl-luster pigment.

Particularly preferred embodiment forms of the invention are hairwaxes containing a combination of either (a) 35 to 39 percent by weight polyethylene glycol with a molecular weight of 4000,
(b) 11 to 18 percent by weight hydrogenated castor oil which is ethoxylated with 40 to 45 moles ethylene oxide,
(c) 39 to 46 percent by weight glycerol and/or ethyl hexanediol and/or polyethylene glycol with a molecular weight of 200 and
(d) 2 to 8 percent by weight water or a combination of (a) 10 to 25 percent by weight polyethylene glycol with a molecular weight of 4000,
(b) 11 to 18 percent by weight hydrogenated castor oil which is ethoxylated with 40 to 60 moles ethylene oxide,
(c) 39 to 46 percent by weight glycerol and/or ethyl hexanediol and/or polyethylene glycol with a molecular weight of 200,
(d) 2 to 12 percent by weight water and
(e) 10 to 20 percent by weight of a pearl-luster pigment.

Due to its waxlike consistency and its "adhesive" (i.e. cohesive) properties, the hairwax, according to the invention, enables an individual hairstyling and the treatment of individual strands of hair. For example, individual strands of hair can be treated with this hairwax in the same manner as with the previously conventional hairwaxes, so that they stand up from the scalp permanently and resiliently. Hair treated in this way is distinguished by a pronounced luster and a high stability of shape of the styled hair. Compared with the previously conventional hairwaxes based on hydrocarbons, however, the decisive advantage of the hairwax, according to the invention, is that the new hairwax can be removed with water easily and completely without residue.

In addition to the constituents (a) to (e) listed above, the hairwax can contain additional ingredients which are conventional and known for such a composition. Examples of such ingredients are perfume oils, active ingredients for the grooming of hair and preservatives such as formaldehyde, salicylic acid, parahydroxy benzoic acid ester, benzoic acid, mandelic acid, polyhexamethylene biguanide hydrochloride or isothiazolinone derivatives. The preservatives can be added to the hairwax in a quantity of approximately 0.01 to 1 percent by weight, while the perfume oils can be contained in the hairwax in a quantity of approximately 0.01 to 2 percent by weight.

In addition, conventional cosmetic hair dyes, such as C.I. Pigment Red 4 (C.I. 12 085), C.I. Pigment Green (C.I. 74 260) and C.I. Vat Blue 4 (C.I. 69 800) and/or pearl-luster pigments, e.g. CTFA-titanium dioxide/mica/iron oxide, CTFA-titanium dioxide/carmine, CTFA-titanium dioxide/mica/iron ferrous cyanide, CTFA-titanium dioxide/mica/chromoxide green, and CTFA-titanium dioxide/mica can be added to the hair wax. The hair dyes are used in a quantity of 0.1 to 6 percent by weight, preferably from 0.5 to 4 percent by weight, while the pearl-luster pigments can be contained in a quantity of 1 to 25 percent by weight, preferably from 10 to 20 percent by weight, in the hairwax, according to the invention.

With such a hairwax it is possible to simultaneously tint the treated hair, so that special fashionable effects, e.g. the tinting of individual strands of hair, can be achieved.

The dyes and pearl-luster pigments, respectively, listed above, as well as other suitable dyestuffs, are described in the Colour Index, 3rd edition, Volume 3, The Society of Dyers and Colourists, Great Britain (1971), and the CTFA-Cosmetic Ingredient Dictionary, 3rd edition, The Cosmetic, Toiletry and Fragrance Association Inc., USA (1982).

The following examples explain the subject matter of the invention is more detail without limiting it to them.

EXAMPLES

Example 1: Hairwax

- 37.5 g polyethylene glycol (M. W. = 4000)
- 26.0 g glycerol
- 20.0 g polyethylene glycol (M. W. = 200)
- 10.8 g hydrogenated castor oil ethoxylated with 40 to 45 moles ethylene oxide (Cremophor ® RH 40, BASF AG)
- 0.3 g perfume oil
- 5.4 g water
- 100.0 g

Example 2: Hairwax

- 39.0 g polyethylene glycol (M. W. = 4000)
- 38.7 g glycerol
- 14.1 g hydrogenated castor oil ethoxylated with 40 to 45 moles ethylene oxide (Cremophor ® RH 40, BASF AG)
- 0.3 g perfume oil
- 7.9 g water
- 100.0 g

Example 3: Hairwax

- 45.0 g ethyl hexanediol
- 35.0 g polyethylene glycol (M. W. = 4000)
- 18.0 g hydrogenated castor oil ethoxylated with 40 to 45 moles ethylene oxide (Cremophor ® RH 40, BASF AG)
- 2.0 g water
- 100.0 g

Example 4: Hairwax which tints the hair red

- 42.6 g glycerol
- 35.0 g polyethylene glycol (M. W. = 4000)
- 11.7 g hydrogenated castor oil ethoxylated with 40 to 45 moles ethylene oxide (Cremophor ® RH 40, BASF AG)
- 2.5 g C. I. Pigment Red 4 (C. I. 12 085)
- 8.2 g water
- 100.0 g

Example 5: Hairwax which tints the hair green

- 35.0 g polyethylene glycol (M. W. = 4000)
- 25.4 g glycerol
- 20.0 g ethyl hexanediol
- 11.7 g hydrogenated castor oil ethoxylated with 40 to 45 moles ethylene oxide (Cremophor ® RH 40, BASF AG)
- 2.5 g C. I. Pigment Green (C. I. 74260)
- 5.4 g water
- 100.0 g

Example 6: Hairwax which tints the hair blue

- 42.2 g polyethylene glycol (M. W. = 200)
- 37.0 g polyethylene glycol (M. W. = 4000)
- 16.2 g hydrogenated castor oil ethoxylated with 40 to 45 moles ethylene oxide (Cremophor ® RH 40, BASF AG)
- 2.8 g C. I. Vat Blue 4 (C. I. 69 800)
- 1.8 g water
- 100.0 g

Example 7: Hairwax which gives the hair a red pearly luster

- 31.76 g polyethylene glycol (M. W. = 200)
- 14.40 g polyethylene glycol (M. W. = 4000)
- 13.84 g glycerol
- 12.00 g hydrogenated castor oil ethoxylated with 40 to 45 moles ethylene oxide (Cremophor ® RH 40, BASF AG)
- 20.00 g CTFA - titanium dioxide/mica/carmine (Colorona ® Carmine Red No. 17272, E. Merck, Darmstadt)
- 8.00 g water
- 100.0 g

Example 8: Hairwax which gives the hair a golden pearly luster

- 31.76 g polyethylene glycol (M. W. = 200)
- 14.40 g polyethylene glycol (M. W. = 4000)
- 13.84 g glycerol
- 12.00 g hydrogenated castor oil ethoxylated with 40 to 45 moles ethylene oxide (Cremophor ® RH 40, BASF AG)
- 20.00 g CTFA - titanium dioxide/mica/iron oxide (Timiron ® Gold Plus MP = 25 No. 17 221, E. Merck, Darmstadt)
- 8.00 g water
- 100.0 g The production of the hairwaxes, according to Examples 1 to 8, is effected in that the constituents are melted at 65° C. and mixed together. The homogeneous melt is then cooled to 40° C. and poured in crucibles.

EXAMPLE 7: COMPARISON TEST

A hairwax which can be rinsed out with water according to Example 3 was compared on 14 dark-haired test subjects in the paired comparison test with a water-soluble hair pomade, according to Hugo Janistyn, "Handbook of Cosmetics ad Scents, Volume III", page 325 (1973), with the following composition

- 60 g polyethylene glycol (M. W. = 4000)
- 40 g ethyl hexanediol
- 100 g.

The hair was first washed and parted in the middle after subsequent drying. One half of the hair was treated with a hair wax according to Example 3 (preparation A) and the other half with the same quantity of the aforementioned hair pomade according to Hugo Janistyn (preparation B).

The results of the subsequent judging carried out with reference to hairstyling technique are compiled in the following tables.

TABLE I

| | Application properties | | | |
| --- | --- | --- | --- | --- |
| | (Number of test persons) | | | |
| Evaluation | very good | good | satisfactory | unsatisfactory |
| Preparation A | 9 | 3 | 2 | 0 |
| Preparation B | 0 | 7 | 7 | 0 |

TABLE II

| | Hairstyling/hold and resiliency of hairstyle | | | |
| --- | --- | --- | --- | --- |
| | (Number of test persons) | | | |
| Evaluation | very good | good | satisfactory | unsatisfactory |
| Preparation A | 10 | 3 | 1 | 0 |
| Preparation B | 0 | 6 | 8 | 0 |

TABLE III

| | Luster | | | |
| --- | --- | --- | --- | --- |
| | (Number of test persons) | | | |
| Evaluation | very good | good | satisfactory | unsatisfactory |
| Preparation A | 12 | 2 | 0 | 0 |
| Preparation B | 0 | 4 | 1 | 9 |

As can be seen from Tables I to III, the hairwax, according to the invention, (which can be rinsed out easily with water) is clearly superior to the water-soluble hair pomade known from the literature on the subject with respect to luster and hairstyling as well as with respect to application properties.

Without further analysis, the foregoing will so fully reveal the gist of the present invention that others can, by applying current knowledge, readily adapt it for various applications without omitting features that, from the standpoint of the prior art, fairly constitute essential characteristics of the generic or specific aspects of this invention.

What is claimed as new and desired to be protected by Letters Patent is set forth in the appended claims:

1. Hairwax, comprising a combination of
   (a) 10 to 41 percent by weight polyethylene glycol with a molecular weight of 3000 to 5000,
   (b) 8 to 25 percent by weight hydrogenated castor oil which is ethoxylated with 40 to 60 moles ethylene oxide,
   (c) 36 to 51 percent by weight glycerol and/or ethyl hexanediol and/or polyethylene glycol with a molecular weight of 100 to 300 and
   (d) 0 to 15 percent by weight water.

2. Hairwax, comprising a combination of
   (a) 32 to 41 percent by weight polyethylene glycol with a molecular weight of 3000 to 5000,
   (b) 8 to 25 percent by weight hydrogenated castor oil which is ethoxylated with 40 to 45 moles ethylene oxide,
   (c) 36 to 51 percent by weight glycerol and/or ethyl hexanediol and/or polyethylene glycol with a molecular weight of 100 to 300 and
   (d) 0 to 10 percent by weight water.

3. Hairwax, comprising a combination of
   (a) 35 to 39 percent by weight polyethylene glycol with a molecular weight of 4000,
   (b) 11 to 18 percent by weight hydrogenated castor oil which is ethoxylated with 40 to 45 moles ethylene oxide,
   (c) 39 to 46 percent by weight glycerol and/or ethyl hexanediol and/or polyethylene glycol with a molecular weight of 200 and
   (d) 2 to 8 percent by weight water.

4. Hairwax according to claim 3, comprises 0.1 to 6 percent by weight of a cosmetic hair dye.

5. Hairwax according to claim 4, wherein said cosmetic hair dye is selected from the group consisting of C.I. Pigment Red 4 (C.I. 12 085), C.I. Pigment Green (C.I. 74 260) and C.I. Vat Blue 4 (C.I. 69 800).

6. Hairwax according to claim 5, comprising 1 to 25 percent by weight of a pearl-luster pigment.

7. Hairwax, comprising a combination of
   (a) 10 to 32 percent by weight polyethylene glycol with a molecular weight of 3000 to 5000,
   (b) 8 to 25 percent by weight hydrogenated castor oil which is ethoxylated with 40 to 60 moles ethylene oxide,
   (c) 36 to 51 percent by weight glycerol and/or ethyl hexanediol and/or polyethylene glycol with a molecular weight of 100 to 300,
   (d) 0 to 15 percent by weight water and
   (e) 5 to 25 percent by weight of a pearl-luster pigment.

8. Hairwax, comprising a combination of
   (a) 10 to 25 percent by weight polyethylene glycol with a molecular weight of 4000,
   (b) 11 to 18 percent by weight hydrogenated castor oil which is ethoxylated with 40 to 45 moles ethylene oxide,
   (c) 39 to 46 percent by weight glycerol and/or ethyl hexanediol and/or polyethylene glycol with a molecular weight of 200,
   (d) 2 to 12 percent by weight water and
   (e) 10 to 20 percent by weight of a pearl-luster pigment.

9. Hairwax according to claim 8, wherein said pearl-luster pigment is selected from the group consisting of CTFA-titanium dioxide/mica/iron oxide, CTFA-titanium dioxide/mica/carmine, CTFA-titanium dioxide/mica/iron ferrous cyanide, CTFA-titanium dioxide/mica/chromoxide green, and CTFA-titanium dioxide/mica.

10. Hairwax, comprising a combination of
    (a) 10 to 41 percent by weight polyethylene glycol with a molecular weight of 3000 to 5000,
    (b) 8 to 25 percent by weight hydrogenated castor oil which is ethoxylated with 40 to 60 moles ethylene oxide,
    (c) 36 to 51 percent by weight glycerol and/or ethyl hexanediol and/or polyethylene glycol with a molecular weight of 100 to 300,
    (d) 0 to 15 percent by weight water, and
    (e) 0.1 to 6 percent by weight of cosmetic hair dye.

11. Hairwax, comprising a combination of
    (a) 32 to 41 percent by weight polyethylene glycol with a molecular weight of 3000 to 5000,
    (b) 8 to 25 percent by weight hydrogenated castor oil which is ethoxylated with 40 to 60 moles ethylene oxide,
    (c) 36 to 51 percent by weight glycerol and/or ethyl hexanediol and/or polyethylene glycol with a molecular weight of 100 to 300,
    (d) 0 to 10 percent by weight water, and
    (e) 0.1 to 6 percent by weight of cosmetic hair dye.

12. Hairwax, comprising a combination of
    (a) 10 to 41 percent by weight polyethylene glycol with a molecular weight of 3000 to 5000,
    (b) 8 to 25 percent by weight hydrogenated castor oil which is ethoxylated with 40 to 60 moles ethylene oxide, (c) 36 to 51 percent by weight glycerol and/or ethyl hexanediol and/or polyethylene glycol with a molecular weight of 100 to 300,
(d) 0 to 15 percent by weight water, and
(e) 1 to 25 percent by weight of a pearl-luster pigment.

13. Hairwax, comprising a combination of
(a) 32 to 41 percent by weight polyethylene glycol with a molecular weight of 3000 to 5000,
(b) 8 to 25 percent by weight hydrogenated castor oil which is ethoxylated with 40 to 45 moles ethylene oxide,
(c) 36 to 51 percent by weight glycerol and/or ethyl hexanediol and/or polyethylene glycol with a molecular weight of 100 to 300,
(d) 0 to 10 percent by weight water, and
(e) 1 to 25 percent by weight of a pearl-luster pigment.

14. Hairwax, comprising a combination of
(a) 35 to 39 percent by weight polyethylene glycol with a molecular weight of 4000,
(b) 11 to 18 percent by weight hydrogenated castor oil which is ethoxylated with 40 to 45 moles ethylene oxide,
(c) 39 to 46 percent by weight glycerol and/or ethyl hexanediol and/or polyethylene glycol with a molecular weight of 200,
(d) 2 to 8 percent by weight water, and
(e) 1 to 25 percent by weight of a pearl-luster pigment.

15. Hairwax according to claim 4, comprising 1 to 25 percent by weight of a pearl-luster pigment.

16. Hairwax according to claim 6, wherein said pearl-luster pigment is selected from the group consisting of CTFA-titanium dioxide/mica/iron oxide, CTFA-titanium dioxide/mica/carmine, CTFA-titanium dioxide/mica/iron ferrous cyanide, CTFA-titanium dioxide/mica/chromoxide green, and CTFA-titanium dioxide/mica.

17. Hairwax according to claim 7, wherein said pearl-luster pigment is selected from the group consisting of CTFA-titanium dioxide/mica/iron oxide, CTFA-titanium dioxide/mica/carmine, CTFA-titanium dioxide/mica/iron ferrous cyanide, CTFA-titanium dioxide/mica/chromoxide green, and CTFA-titanium dioxide/mica.

* * * * *